United States Patent [19]

Doyle

[11] 4,385,005
[45] May 24, 1983

[54] PROCESS FOR SEPARATING UNSATURATED HYDROCARBONS USING COPPER OR SILVER COMPLEXES WITH FLUORINATED DIKETONATES

[75] Inventor: Gerald Doyle, Whitehouse Station, N.J.

[73] Assignee: Exxon Research and Engineering Co., Florham Park, N.J.

[21] Appl. No.: 282,653

[22] Filed: Jul. 13, 1981

[51] Int. Cl.³ .................. C07C 119/02; C07C 7/12; C07C 121/46
[52] U.S. Cl. .................. 260/464; 260/405.5; 260/465 R; 260/465 K; 260/465.9; 423/245; 560/104; 560/191; 560/218; 562/600; 568/324; 568/438; 585/843; 585/844; 585/845
[58] Field of Search ............... 260/465 K, 465 R, 464, 260/465.9; 585/843–845; 423/245; 560/104, 191, 218; 562/600; 568/324, 438

[56] References Cited

U.S. PATENT DOCUMENTS

| | | | |
|---|---|---|---|
| 3,401,112 | 9/1968 | Dunlop et al. | 208/308 |
| 3,517,079 | 6/1970 | Beckham | 260/674 |
| 3,700,416 | 10/1972 | Lucid | 23/312 |
| 3,754,047 | 8/1973 | Long et al. | 260/677 |
| 3,755,487 | 8/1973 | Jahnig et al. | 260/677 |
| 4,279,874 | 7/1981 | Doyle | 423/246 |

OTHER PUBLICATIONS

W. Partenheimer et al., "The Synthesis of Some New Silver Olefin Compounds of the Type (Olefin) (β–diketonato)silver(I)", Inorg. Chem., 11, 2840-2841 (1972).

Bedford et al., Reactions of 1,4-Diazabicyclo [2.2.2] Octane with Bis-[1,1,1,5,5,5,-hexafluoropentane-2,4-dionato] Cu(II), J.C.S. Dalton, 2208 (1972).

Bailey et al., Ternary Complexes of Cu(II) with Mixed Acetylacetonate and Nitrogen-containing Ligands, J.C.S. Dalton, 984 (1980).

*Primary Examiner*—Dolph H. Torrence
*Attorney, Agent, or Firm*—James H. Takemoto

[57] ABSTRACT

A process of removing unsaturated hydrocarbons containing at least one non-aromatic unsaturation from feedstreams which comprises contacting the feedstream with at least one of $Cu_2O$ or $Ag_2O$ and a fluorinated acetylacetonate of the formula

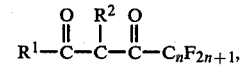

where $R^1$ is $C_1$–$C_6$ fluoroalkyl, $C_1$–$C_8$ alkyl, $C_4$–$C_6$ heterocycle containing O, S or N or $C_6$–$C_{10}$ aryl, $R^2$ is H or $C_1$–$C_6$ alkyl with the proviso that $R^1$ and $R^2$ together with the carbons to which they are attached may be joined together to form a $C_6$ ring and n is from 1 to 8, in an inert organic solvent.

21 Claims, No Drawings

PROCESS FOR SEPARATING UNSATURATED HYDROCARBONS USING COPPER OR SILVER COMPLEXES WITH FLUORINATED DIKETONATES

BACKGROUND OF THE INVENTION

This invention relates to the formation of new copper or silver complexes containing a fluorinated diketonate and unsaturated hydrocarbons as ligands. More particularly, unsaturated hydrocarbons can be removed from feedstreams by reaction with $Cu_2O$ or $Ag_2O$ and beta-diketonates to form the copper or silver complexes.

It is known that certain silver(I) and copper(I) salts form complexes with olefins and acetylenes. For example, cuprous chloride is known to form complexes with both ethylene and acetylene. U.S. Pat. No. 3,401,112 teaches a method of separating a mixture of hydrocarbons having differing degrees of unsaturation using a copper(I) salt of the formula CuXA where XA is an anion, X is oxygen or fluorine and A is the remainder of the anion. Examples of fluorinated anions include fluoro substituted carboxylates, fluorosulphonate, perfluoroborate, hexafluorophosphate and hexafluoroantimonate. CuXA forms a cuprous complex with said unsaturated hydrocarbon. Similarly, U.S. Pat. No. 3,517,079 describes a process for separating vinyl aromatic hydrocarbons from alkyl aromatic hydrocarbons using a cuprous fuoroborate or cuprous fluorophosphate salt wherein a complex is formed. U.S. Pat. Nos. 3,754,047 and 3,755,487 disclose a process for separating complexible ligands such as olefins, acetylenes, aromatics and CO from a feedstream using cuprous salts such as $CuAlCl_4$, $CuBF_4$, $CuOOCCF_3$, $CuPF_6$ and the like.

SUMMARY OF THE INVENTION

It has been discovered that copper(I) and silver(I) can form a new class of complexes with fluorinated acetylacetonate anions and unsaturated hydrocarbons as ligands. The complexes of the invention have the formula

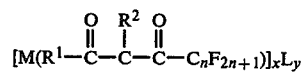

where M is Cu(I) or Ag(I); $R^1$ is $C_1-C_6$ fluoroalkyl, $C_1-C_8$ alkyl, $C_4-C_6$ heterocycle containing O, S or N or $C_6-C_{10}$ aryl; $R^2$ is H or $C_1-C_6$ alkyl with the proviso that $R^1$ and $R^2$ together with the carbons to which they are attached may be joined together to form a $C_6$ ring; L is an unsaturated hydrocarbon containing at least one non-aromatic unsaturation capable of forming a Cu-L bond, preferably an unsaturated hydrocarbon containing at least one ethylenic, acetylenic or isonitrilic unsaturation; x and y are 1 or 2; and n is an integer from 1 to 8.

The present invention also relates to the discovery that unsaturated hydrocarbons containing at least one non-aromatic unsaturation can be removed from feedstreams by a process which comprises contacting the feedstream with $Cu_2O$ or $Ag_2O$ and a fluorinated acetylacetonate of the formula

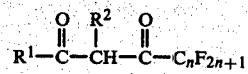

where $R^1$ is $C_1-C_6$ fluoroalkyl, $C_1-C_8$ alkyl, $C_4-C_6$ heterocycle containing O, S or N or $C_6-C_{10}$ aryl, $R^2$ is H or $C_1-C_6$ alkyl with the proviso that $R^1$ and $R^2$ together with the carbons to which they are attached may be joined together to form a $C_6$ ring, and n is an integer from 1 to 8, in an inert organic solvent.

In another embodiment, unsaturated hydrocarbons containing at least one non-aromatic unsaturation can be removed from feedstreams by a process which comprises contacting the feedstream with Cu metal and Cu(III) fluorinated acetylacetonate of the formula

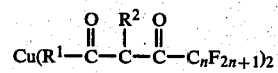

where $R^1$ is $C_1-C_6$ fluoroalkyl, $C_1-C_8$ alkyl, $C_4-C_6$ heterocycle containing O, S or N or $C_6-C_{10}$ aryl, $R^2$ is H or $C_1-C_6$ alkyl with the proviso that $R^1$ and $R^2$ together with the carbons to which they are attached may be joined together to form a $C_6$ ring and n is an integer from 1 to 8, in an inert organic solvent. Alternatively, the unsaturated hydrocarbons can be removed from feedstreams by contacting the feedstreams with a Ag(I) fluorinated acetylacetonate of the formula

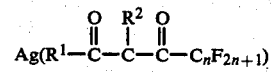

where $R^1$, $R^2$ and n are defined as above, in an inert organic solvent.

DETAILED DESCRIPTION OF THE INVENTION

Complexes of the formula

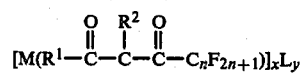

are prepared by reacting metal oxide, fluorinated acetylacetonate and unsaturated hydrocarbon in an inert organic solvent, and this reaction forms the basis for the present invention for removal of unsaturated hydrocarbons from gas streams. The reaction is illustrated as follows:

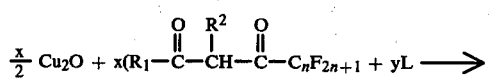

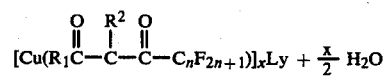

When

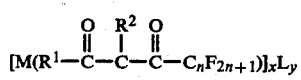

is heated in solution, the following equilibria for the respective metals M are established:

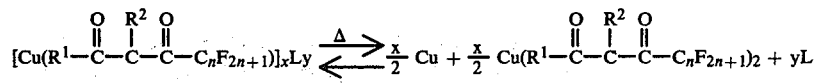

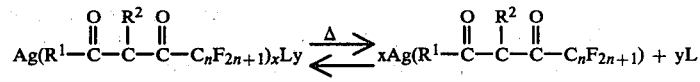

Based on these equilibria, it should also be possible to remove unsaturated hydrocarbons from feedstreams by employing Cu metal plus a Cu(II) fluorinated acetylacetonate or a Ag(I) fluorinated acetylacetonate, and this can be verified experimentally.

Preferred fluorinated acetylacetonate ligands have the formula

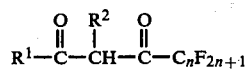

where $R^1$ is $C_1$-$C_3$ fluoroalkyl, especially $CF_3$, $C_1$-$C_6$ alkyl, $C_6$-$C_{10}$ aryl or $C_4$-$C_5$ heterocycle containing O, S or N, $R^2$ is H with the proviso that $R^1$ and $R^2$ may join together to form a $C_6$ ring and n is 1 to 4, especially 1. Examples of preferred embodiments of fluorinated acetylacetonate ligands include 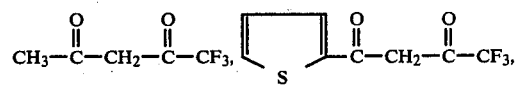

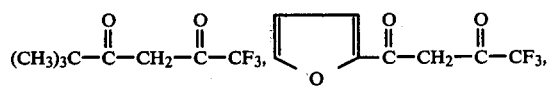

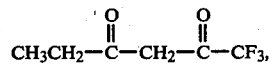

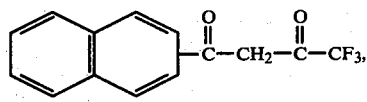

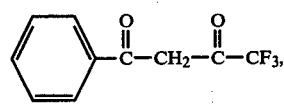

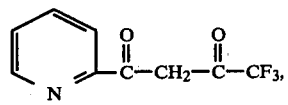

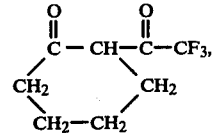

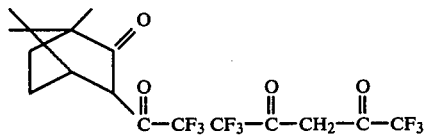

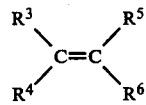

is especially preferred.

Preferred unsaturated hydrocarbons are (a) alkenes of the formula

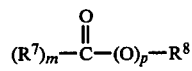

where each $R^3$-$R^6$ is independently H; $C_1$-$C_{30}$, more preferably $C_1$-$C_{15}$ and especially $C_1$-$C_8$ aliphatic with the proviso that any combination of $R^3$, $R^4$, $R^5$ and $R^6$ may be joined together to form at least one $C_4$-$C_{14}$, more preferably $C_5$-$C_{12}$, most preferably $C_6$-$C_8$ cycloaliphatic ring; —C≡N; $C_6$-$C_{10}$ aryl; $C_7$-$C_{14}$ araliphatic;

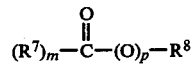

where m and p are 0 or 1, $R^7$ is $C_1$-$C_{20}$, preferably $C_1$-$C_{10}$ aliphatic, and $R^8$ is H, $C_1$-$C_{10}$ aliphatic or $C_6$-$C_{10}$ aryl with the proviso that adjacent $$(R^7)_m-\overset{\overset{O}{\|}}{C}-(O)_p-R^8$$

may be joined together to form a $C_4$-$C_{16}$ anhydride; (b) alkynes of the formula $R^9$—C≡C—$R^{10}$ where $R^9$ and $R^{10}$ are independently H; $C_1$-$C_{30}$, more preferably $C_1$-$C_{15}$ and especially $C_1$-$C_8$ aliphatic; $C_6$-$C_{10}$ aryl or $C_7$-$C_{14}$ araliphatic; or (c) isonitriles of the formula $R^{11}$—N≡C where $R^{11}$ is $C_1$-$C_{20}$ aliphatic; $C_3$-$C_{10}$ cycloaliphatic; $C_7$-$C_{20}$ araliphatic or $C_6$-$C_{10}$ aryl. The unsaturated hydrocarbons may be substituted with unreactive substituents such as halogen, cyano, alkoxy, nitro and the like.

Examples of suitable unsaturated ligands include: ethylene, acetylene, 1-octene, isobutylene, 1,5-cyclooctadiene, stilbene, diphenylacetylene, styrene, cyclooctene, 1,5,9-cyclododecatriene, 1,3-hexadiene, isopropylacetylene, 1-decene, 1,5-bicyclophetadiene, 1-octadecene, cyclopentene, octalin, methylene cyclohexane, diphenyl fulvene, 1-octadecyne, benzyl cinnamate, benzal acetophenone, acrolein, acrylonitrile, maleic anhydride, oleic acid, linolenic acid, acrylic acid, methyl methacrylate and diethyl maleate. Suitable isonitriles are, e.g., methyl isocyanide, butyl isocyanide, cyclohexyl, isocyanide, phenylethyl isocyanide and phenyl isocyanide.

Examples of copper(I) and silver(I) complexes formed by unsaturated hydrocarbon removal from gas streams are as follows. Cu(1,5-cyclooctadiene)

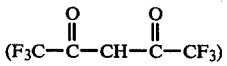

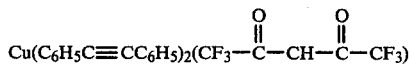

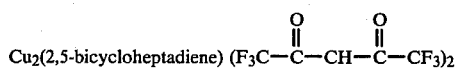

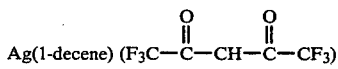

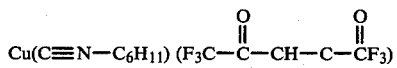

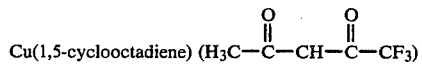

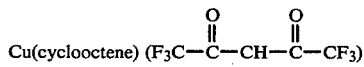

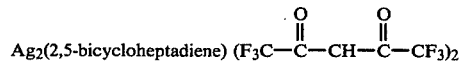

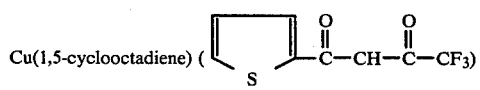

The process of the invention takes place in an inert organic solvent. Preferred solvents are ethers, ketones, esters, alcohols, saturated aliphatic hydrocarbons, aromatic hydrocarbons and the like. It is necessary that the amounts of CO in the reaction mixture not exceed about 10 vol.%. CO competes with unsaturated hydrocarbon ethylene complexes are rather unstable due to a high dissociative pressure and heating would not be desirable. On the other hand, higher molecular weight olefins result in stable compounds and the reaction mixture can be heated without harmful results with respect to the removal of unsaturated hydrocarbon.

$Cu_2O$ and/or $Ag_2O$ and fluorinated acetylacetonate are usually present in the reaction mixture in approximately stoichiometric amounts. Wide variations, however, are possible. The concentrations of metal oxide and fluorinated acetylacetonate may range from about 0.001 to 5 M, preferably 0.1 to 3 M. The feedstream containing unsaturated hydrocarbons is contacted with the reaction mixture in either a batchwise or continuous mode. In the case of a gaseous feedstream, the gas may be introduced into the reaction mixture through a gas dispersion device. Liquid feedstreams may be conducted to a stirred reaction vessel or the separation process may be carried out in a countercurrent extractor.

A continuous mode of operation is preferred. Using any of the separation reactions described hereinbefore, a solution containing the complex

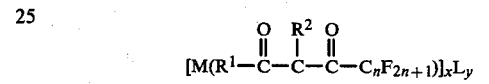

where M, $R^1$, $R^2$, L, x, y and n are defined above is formed. This solution is subjected to heating at temperatures sufficient to decompose the complex, and the unsaturated hydrocarbon separated from solution, e.g., by distillation. The temperature required for decomposition will vary according to the stability of the complex and varies from 0° to 200° C. Depending on the choice of solvent, elevated pressures may be required to maintain the inert organic solvent as a liquid. Decomposition products are either Cu metal and Cu(II) fluorinated acetylacetonate or Ag(I) fluorinated acetylacetonate depending on whether M above is Cu or Ag. The resultant mixture or solution is recycled and further contacted with feedstream thus reforming the metal complex and then re-heated to decomposition temperatures. This cyclical process is represented by the following equilibria:

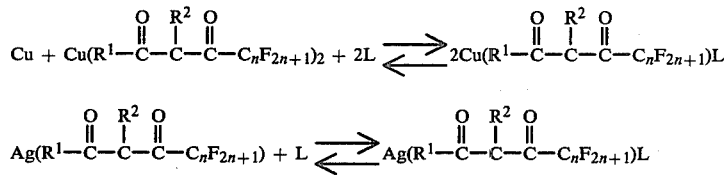

in the formation of cuprous complex and based on thermodynamic considerations, a CO complex forms in preference to the unsaturated hydrocarbon complex as long as competing amounts of CO are present. It is also desirable to carry the process in an inert atmosphere, since gases such as oxygen may result in the oxidation of Cu(I) to Cu(II).

Reaction times are not critical. Generally, the reaction mixture is stirred until a clear solution is obtained. A solid product may then be isolated by evaporating solvent. Suitable temperatures are from about −100° to +100° C. with room temperature being preferred. If the reaction mixture is heated excessively, it is possible that a dissociative reaction may take place. Thus, copper (I)

Gas feedstreams may contain other gases such as $N_2$, $H_2$, $CO_2$, alkanes, $H_2O$, $SO_2$, $SO_3$, and $NH_3$. The feedstream should not, however, contain $H_2S$ or CO in amounts $> \sim 10$ vol.%, and $O_2$ amounts should not exceed about 10 vol.%. Liquid feedstreams may contain mixtures of organic solvents.

The process of the invetion may be used to separate unsaturated hydrocarbons containing at least one non-aromatic unsaturation from gas and liquid feedstreams including those containing aromatic hydrocarbons. The process may also be used to separate optical isomers. If an optically active fluorinated acetylacetonate e.g., 3-trifluoroacetyl-d-camphor, is reacted with an unsaturated ligand which is a racemic mixture, a mixture of diastereoisomers is formed. By using known resolution techniques for separating the diastereoisomers, optically pure unsaturated ligands may be isolated.

The present process is further illustrated by the following examples.

EXAMPLE 1

A suspension of 1.43 g (0.01 mole) cuprous oxide in 75 ml tetrahydrofuran was stirred with 2.16 g (0.02 mole) of 1,5-cyclooctadiene in a 250 ml flask under nitrogen. A solution of 4.16 g (0.02 mole) 1,1,1,5,5,5-hexafluoroacetylacetone (hfacac) in 50 ml tetrahydrofuran was added dropwise over a 30 minute period. Red $Cu_2O$ gradually dissolved forming a clear yellow solution. The solution was filtered to remove any remaining solids and the solvent was then removed on a rotary evaporator. Cu(1,5-COD)(hfacac) was obtained as bright yellow crystals which could be purified by recrystallization from hexane. The product was characterized by IR and NMR spectroscopy and elemental analysis.

EXAMPLE 2

A suspension of 10 mmole $Cu_2O$ in 100 ml tetrahydrofuran was prepared and 20mmole hexafluoroacetylacetone was added to this mixture. After stirring, a gaseous mixture with the approximate composition 40% $H_2$, and 60% $C_2H_4$ was bubbled through the solution at room temperature and a complex was formed with an ethylene:Cu(I) salt ratio of 1:1. Analysis of the gas mixture over the solution indicated an essentially complete removal of ethylene.

In order to recover ethylene, $N_2$ was passed through the solution. Alternatively, the solution was heated to 50° C. until ethylene evolution ceased.

EXAMPLE 3

The procedure of Example 1 was repeated except that tetrahydrofuran is replaced with a solvent mixture of 90 ml of tetrahydrofuran and 10 ml water. Identical results were obtained showing that the absorption of ethylene is not appreciably affected by relatively large amounts of water.

EXAMPLE 4

The procedure of Example 1 was repeated except that the gaseous mixture bubbled through the Cu(I) salt solution contained about 50% propane and 50% propylene. An analysis of the solution and gas mixture over the solution indicated the formation of a 1:1 propylene-Cu(I) complex and the nearly complete removal of propylene from the gas. This demonstrates that the absorption of olefins can take place in the presence of relatively large amounts of alkanes.

EXAMPLE 5

A suspension of 10 mmole $Cu_2O$ in 100 ml methylene chloride was prepared and 20 mmole hexafluoroacetylacetone added to the mixture. A gas stream containing approximately 50% ethylene and 50% nitrogen was passed through the solution forming the 1:1 ethylene:-Cu(I) salt. Heating the mixture to reflux resulted in the liberation of the ethylene and the formation of copper metal and copper II hexafluoroacetylacetone. This mixture was cooled to room temperature and again exposed to the ethylenenitrogen gas mixture which resulted in the formation of the 1:1 ethylene:Cu(I) salt. Heating to reflux again liberates ethylene and this cyclic process can be repeated indefinitely.

EXAMPLES 6–45

The examples shown in the following table further illustrates the types of unsaturated ligands which can be removed from feedstreams and the particular complexes formed thereby.

TABLE I

| Ex. No. | Ligand (mmol) | β-diketone (mmol) | Metal Oxide (mmol) | Solvent | Compound Formed |
|---|---|---|---|---|---|
| 6 | 1,5-cyclooctadiene (COD) (9.0) | thenoyltrifluoroacetylacetone (TTA) (14.0) | $Cu_2O$ (9.0) | $CH_2Cl_2$ | Cu(COD)TTA |
| 7 | 1,5-cyclooctadiene (20.0) | hexafluoroacetylacetone (hfacac) (18.0) | $Cu_2O$ (11.0) | $C_6H_5CH_3$ | Cu(COD)hfacac |
| 8 | 1,3-butadiene (large excess) | hexafluoroacetylacetone (14.0) | $Cu_2O$ (7.0) | THF | Cu($C_4H_6$)hfacac* |
| 9 | Diphenylacetylene (9.65) | hexafluoroacetylacetone (4.81) | $Cu_2O$ (3.0) | $CH_2Cl_2$ | Cu($\phi$C≡C$\phi$)$_2$hfacac |
| 10 | Diphenylacetylene (9.65) | trifluoroacetylacetone (tfacac) (4.80) | $Cu_2O$ (3.0) | $CH_2Cl_2$ | Cu($\phi$C≡C$\phi$)$_2$tfacac |
| 11 | 1,5-cyclooctadiene (20.0) | trifluoroacetylacetone (18.0) | $Cu_2O$ (11.0) | $CH_2Cl_2$ | Cu(COD)tfacac |
| 12 | Bicyclo[2.2.1]hepta-2,5-diene (22.0) | hexafluoroacetylacetone (21.0) | $Cu_2O$ (11.0) | $CH_2Cl_2$ | [Cu(hfacac)]$_2$  |
| 13 | cyclohexylisonitrile (13.0) | hexafluoroacetylacetone (6.0) | $Cu_2O$ (3.0) | $CH_2Cl_2$ | Cu(C≡N—)hfacac |
| 14 | Bicyclo[2.2.1]-2-heptene (18.0) | hexafluoroacetylacetone (17.0) | $Cu_2O$ (11.0) | $CH_2Cl_2$ | Cu()hfacac |
| 15 | 1,3,5,7-cyclooctatetraene (7.5) | trifluoroacetylacetone (7.1) | $Cu_2O$ (4.0) | $CH_2Cl_2$ | Cu(COT)tfacac |

TABLE I-continued

| Ex. No. | Ligand (mmol) | β-diketone (mmol) | Metal Oxide (mmol) | Solvent | Compound Formed |
|---|---|---|---|---|---|
| 16 | 1,3,5,7-cyclo-octatetraene (3.6) | trifluoroacetyl-acetone (7.2) | $Cu_2O$ (4.0) | $CH_2Cl_2$ | [Cu(tfacac)]$_2$COT |
| 17 | 2-hexyne (5.0) | hexafluoroacetyl-acetone (4.3) | $Cu_2O$ (2.5) | $CH_2Cl_2$ | Cu(CH$_3$C≡CC$_3$H$_7$)hfacac |
| 18 | styrene (11.5) | hexafluoroacetyl-acetone (9.61) | $Cu_2O$ (5.00) | $CH_2Cl_2$ | Cu(CH$_2$=CH—φ)hfacac |
| 19 | isoprene (15.0) | hexafluoroacetyl-acetone (7.3) | $Cu_2O$ (4.0) | $CH_2Cl_2$ | Cu(CH$_2$=C(CH$_3$)—CH=CH$_2$)hfacac |
| 20 | ethylene (large excess) | hexafluoroacetyl-acetone (6.9) | $Cu_2O$ (3.5) | $CH_2Cl_2$ | Cu(CH$_2$=CH$_2$)hfacac* |
| 21 | 2,8-decadiyne (15.0) | hexafluoroacetyl-acetone (14.0) | $Cu_2O$ (8.0) | $CH_2Cl_2$ | Cu(hfacac)]$_2$CH$_3$C≡C—(CH$_2$)$_4$C≡CCH$_3$ |
| 22 | 1,5-cycloocta-diene (4.5) | 3-trifluoroacetyl-d-camphor (TAC) (4.0) | $Cu_2O$ (2.0) | $CH_2Cl_2$ | Cu(COD)(TAC) |
| 23 | cyclohexene (27.0) | hexafluoroacetyl-acetone (12.0) | $Cu_2O$ (7.0) | $CH_2Cl_2$ | Cu(cyclohexene)hfacac |
| 24 | Bicyclo[2.2.1]-2-heptene (14.0) | trifluoroacetyl-acetone (13.0) | $Cu_2O$ (6.5) | $CH_2Cl_2$ | Cu(norbornene)tfacac |
| 25 | cyclohexyliso-nitrile (16.0) | trifluoroacetyl-acetone (8.2) | $Cu_2O$ (15.0) | $CH_2Cl_2$ | Cu(C≡N—C$_6$H$_{11}$)tfacac |
| 26 | phenylacetylene (15.0) | hexafluoroacetyl-acetone (15.0) | $Cu_2O$ (8.0) | $CH_2Cl_2$ | Cu(φC≡CH)hfacac |
| 27 | cyclooctene (COE) (9.07) | hexafluoroacetyl-acetone (9.0) | $Cu_2O$ (4.6) | $CH_2Cl_2$ | Cu(COE)hfacac |
| 28 | propene (large excess) | hexafluoroacetyl-acetone (6.9) | $Cu_2O$ (3.5) | $CH_2Cl_2$ | Cu(CH$_3$CH=CH$_2$)hfacac* |
| 29 | 1-decene (24.0) | hexafluoroacetyl-acetone (24.0) | $Cu_2O$ (14.0) | $CH_2Cl_2$ | Cu(CH$_2$=CH—C$_8$H$_{17}$)hfacac |
| 30 | 3-methylcyclo-hexene (15) | hexafluoroacetyl-acetone (9.0) | $Cu_2O$ (5.0) | $CH_2Cl_2$ | Cu(CH$_3$-cyclohexene)hfacac |
| 31 | 1,3,5,7-cyclo-octatetraene (7.5) | hexafluoroacetyl-acetone (7.2) | $Cu_2O$ (4.0) | $CH_2Cl_2$ | Cu(COT)hfacac |
| 32 | 1,3,5,7-cyclo-octatetraene (3.6) | hexafluoroacetyl-acetone (7.2) | $Cu_2O$ (4.0) | $CH_2Cl_2$ | [Cu(hfacac)]$_2$COT |
| 33 | (+)-α-pinene (7.5) | hexafluoroacetyl-acetone (7.4) | $Cu_2O$ (4.0) | $CH_2Cl_2$ | Cu(α-pinene)hfacac |
| 34 | 3-methyl-cyclo-hexene (8.0) | 3-trifluoroacetyl-d-camphor (6.0) | $Cu_2O$ (3.5) | $CH_2Cl_2$ | Cu(CH$_3$-cyclohexene)TAC |
| 35 | d,l-α-pinene (8.0) | 3-trifluoroacetyl-d-camphor (6.0) | $Cu_2O$ (3.5) | $CH_2Cl_2$ | Cu(d-α-pinene)TAC + Cu(l-α-pinene)TAC, mixed diastereomers |
| 36 | 1,5-cycloocta-diene (1.12) | hexafluoroacetyl-acetone (1.12) | $Ag_2O$ (0.56) | $CH_2Cl_2$ | Ag(COD)hfacac |
| 37 | ethylene (large excess) | hexafluoroacetyl-acetone (4.28) | $Ag_2O$ (2.16) | $CH_2Cl_2$ | Ag(CH$_2$=CH$_2$)hfacac* |
| 38 | diphenylacetylene (8.64) | hexafluoroacetyl-acetone (4.30) | $Ag_2O$ (2.16) | $CH_2Cl_2$ | Ag(φC≡Cφ)$_2$hfacac |
| 39 | cyclooctene (8.64) | hexafluoroacetyl-acetone (8.64) | $Ag_2O$ (4.37) | $CH_2Cl_2$ | Ag(COE)hfacac |
| 40 | propylene (large excess) | hexafluoroacetyl-acetone (4.28) | $Ag_2O$ (2.16) | $CH_2Cl_2$ | Ag(CH$_3$CH=CH$_2$)hfacac |
| 41 | 1-decene (4.4) | hexafluoroacetyl-acetone (4.3) | $Ag_2O$ (2.2) | $CH_2Cl_2$ | Ag(CH$_2$=CHC$_8$H$_{17}$)hfacac |
| 42 | 1,3-butadiene (large excess) | hexafluoroacetyl-acetone (4.3) | $Ag_2O$ (2.16) | $CH_2Cl_2$ | Ag(CH$_2$=CH—CH=CH$_2$)hfacac* |
| 43 | bicyclo[2.2.1]-2-heptene (4.4) | hexafluoroacetyl-acetone (4.3) | $Ag_2O$ (2.2) | $CH_2Cl_2$ | Ag(norbornene)hfacac |

TABLE I-continued

| Ex. No. | Ligand (mmol) | β-diketone (mmol) | Metal Oxide (mmol) | Solvent | Compound Formed |
|---|---|---|---|---|---|
| 44 | bicyclo[2.2.1]-hepta-2,5-diene (4.4) | hexafluoroacetyl-acetone (4.3) | Ag₂O (2.2) | CH₂Cl₂ | [Ag(hfacac)]₂  |
| 45 | diethyl maleate | hexafluoroacetyl-acetone (20.0) | Cu₂O (10.0) | none | Cu(C₂H₅OC—CH=CH—C—OC₂H₅)hfacac 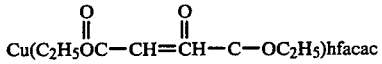 |

*Not stable at room temperature.

What is claimed is:

1. A process for removing unsaturated hydrocarbons containing at least one non-aromatic unsaturation from feedstreams provided that the feedstream shall not contain CO in an amount exceeding about 10 vol. % which comprises contacting the feedstream with at least one of Cu₂O or Ag₂O and a fluorinated acetylacetonate of the formula

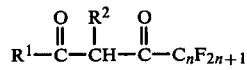

where $R^1$ is $C_1$-$C_6$ fluoroalkyl, $C_1$-$C_8$ alkyl, $C_4$-$C_6$ heterocycle containing O, S, or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an inert organic solvent.

2. A process for removing unsaturated hydrocarbons containing at least one non-aromatic unsaturation from feedstreams provided that the feedstream shall not contain CO in an amount exceeding about 10 vol. % which comprises contacting the feedstream with Cu metal and a Cu(II) fluorinated acetylacetonate in the formula

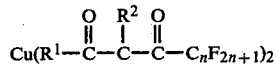

or a Ag(I) fluorinated acetylacetonate of the formula

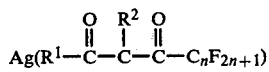

where $R^1$ is $C_1$-$C_6$ fluoroalkyl, $C_1$-$C_8$ alkyl, $C_4$-$C_6$ heterocycle containing O, S or N or $C_6$-$C_{10}$ aryl, $R^2$ is H or $C_1$-$C_6$ alkyl with the proviso that $R^1$ and $R^2$ together with the carbons to which they are attached may be joined together to form a $C_6$ ring and n is an integer from 1 to 8, in an inert organic solvent.

3. The process of claims 1 or 2 wherein $R^1$ is $C_1$-$C_3$ fluoralkyl, $C_1$-$C_6$ alkyl, $C_6$-$C_{10}$ aryl or $C_4$ or $C_5$ heterocycle containing O, S or H.

4. The process of claims 1 or 2 wherein $R^2$ is H.

5. The process of claims 1 or 2 wherein $R^1$ is $CF_3$, $CH_3$ or

6. The process of claims 1 or 2 wherein n is 1.

7. The process of claim 1 wherein M is Cu.

8. The process of claim 1 wherein M is Ag.

9. The process of claims 1 or 2 wherein $R^1$ is $CF_3$ and n is 1.

10. The process of claims 1 or 2 wherein the unsaturated hydrocarbons contains at least one ethylenic or acetylenic unsaturation.

11. The process of claim 1 wherein the amounts of Cu₂O, Ag₂O and fluorinated acetylacetonate are from about 0.001 to 5 M.

12. The process of claim 2 wherein the amounts of Cu metal and Cu(II) fluorinated acetylacetonate or Ag(I) fluorinated acetylacetonate are from about 0.001 to 5 M.

13. The process of claims 1 or 2 wherein the temperature is from about $-100°$ to $+100°$ C.

14. The process of claims 1 or 2 wherein a solution of a Cu(II) or Ag(I) complex with fluorinated acetylacetonate and unsaturated hydrocarbon containing at least one non-aromatic unsaturation is formed.

15. The process of claim 14 wherein the solution is heated to a temperature sufficient to decompose the complex.

16. The process of claim 15 wherein the solution is recycled and further contacted with the feedstream.

17. The process of claims 1 or 2 wherein the alkene is an alkene of the formula

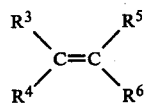

where each $R^3$-$R^6$ is independently H; $C_1$-$C_{30}$ aliphatic with the proviso that any combination of $R^3$, $R^4$, $R^5$ and $R^6$ may be joined together to form at least one $C_4$-$C_{14}$ cycloaliphatic ring; —C≡N; $C_6$-$C_{10}$ aryl; $C_7$-$C_{14}$ araliphatic;

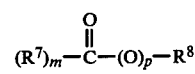

where m and p are 0 or 1, $R^7$ is $C_1$-$C_{20}$ aliphatic and $R^8$ is H, $C_1$-$C_{10}$ aliphatic or $C_6$-$C_{10}$ aryl with the proviso that adjacent

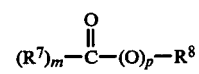

may be joined together to form a $C_4$-$C_{16}$ anhydride.

18. The process of claims 1 or 2 wherein the alkyne is an alkyne of the formula $R^9$—C≡C—$R^{10}$ where $R^9$ and $R^{10}$ are independently H; $C_1$-$C_{30}$ alihatic; $C_6$-$C_{10}$ aryl or $C_7$-$C_{14}$ araliphatic.

19. The process of claims 1 or 2 wherein the isonitrile is an isonitrile of the formula $R^{11}-N\equiv C$ where $R^{11}$ is $C_1-C_{20}$ aliphatic; $C_3-C_{10}$ cycloaliphatic; $C_7-C_{20}$ araliphatic or $C_6-C_{10}$ aryl.

20. A process for removing at least one of alkenes, alkynes or isonitriles from feedstreams provided that the feedstream shall not contain CO in an amount exceeding about 10 vol. % which comprises contacting the feedstream with at least one of $Cu_2O$ or $Ag_2O$ and a fluorinated acetylacetonate of the formula

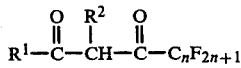

where R is $C_1-C_6$ fluoroalkyl, $C_1-C_8$ alkyl, $C_4-C_6$ heterocycle containing O, S, or N or $C_6-C_{10}$ aryl, $R^2$ is H or $C_1-C_6$ alkyl with the proviso that $R^1$ and $R^2$ together with the carbons to which they are attached may be joined together to form a $C_6$ ring and n is an integer from 1 to 8, in an inert organic solvent.

21. A process for removing at least one of alkenes, alkynes or isonitriles from feedstreams provided that the feedstream shall not contain CO in an amount exceeding about 10 vol. % which comprises contacting the feedstream with Cu metal and a Cu(II) fluorinated acetylacetonate of the formula

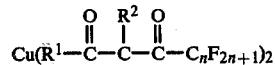

or a Ag(I) fluorinated acetylacetonate of the formula

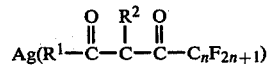

where $R^1$ is $C_1-C_6$ fluoroalkyl, $C_1-C_8$ alkyl, $C_4-C_6$ heterocycle containing O, S or N or $C_6-C_{10}$ aryl, $R^2$ is H or $C_1-C_6$ alkyl with the proviso that $R^1$ and $R^2$ together with the carbons to which they are attached may be joined together to form a $C_6$ ring and n is an integer from 1 to 8, in an inert organic solvent.

* * * * *